United States Patent
Chen et al.

(10) Patent No.: US 8,649,838 B2
(45) Date of Patent: Feb. 11, 2014

(54) WAVELENGTH SWITCHING FOR PULSE OXIMETRY

(75) Inventors: Bo Chen, Louisville, CO (US); Edward M. McKenna, Boulder, CO (US); Youzhi Li, Longmont, CO (US); Daniel Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 602 days.

(21) Appl. No.: 12/888,226

(22) Filed: Sep. 22, 2010

(65) Prior Publication Data

US 2012/0071739 A1 Mar. 22, 2012

(51) Int. Cl.
*A61B 5/1455* (2006.01)

(52) U.S. Cl.
USPC .................. 600/323; 600/310; 600/322

(58) Field of Classification Search
USPC .................................... 600/309–344
See application file for complete search history.

(56) References Cited

U.S. PATENT DOCUMENTS

| | | | |
|---|---|---|---|
| 4,321,930 | A | 3/1982 | Jobsis et al. |
| 4,380,240 | A | 4/1983 | Jobsis et al. |
| 4,805,623 | A | 2/1989 | Jobsis |
| 4,854,699 | A | 8/1989 | Edgar |
| 4,867,557 | A | 9/1989 | Takatani et al. |
| 4,890,619 | A | 1/1990 | Hatschek |
| 4,926,867 | A | 5/1990 | Kanda et al. |
| 5,088,493 | A | 2/1992 | Giannini et al. |
| 5,204,922 | A | 4/1993 | Weir et al. |
| 5,239,185 | A | 8/1993 | Ito et al. |
| 5,297,548 | A | 3/1994 | Pologe |

(Continued)

FOREIGN PATENT DOCUMENTS

| | | |
|---|---|---|
| CA | 2494030 | 2/2004 |
| CN | 2691489 | 4/2005 |

(Continued)

OTHER PUBLICATIONS

Mannheimer, Paul D., et al.; "Wavelength Selection for Low-Saturation Pulse Oximetry," *IEEE Transactions on Biomedical Engineering*, vol. 44, No. 3, Mar. 1997, p. 148-158.

(Continued)

*Primary Examiner* — Eric Winakur
*Assistant Examiner* — Marjan Fardanesh
(74) *Attorney, Agent, or Firm* — Fletcher Yoder (57) ABSTRACT

The present disclosure describes techniques that may provide more accurate estimates of arterial oxygen saturation using pulse oximetry by switching between a wavelength spectrum of at least a first and a second light source so that the arterial oxygen saturation estimates at low (e.g., in the range below 75%), medium (e.g., greater than or equal to 75% and less than or equal to 84%), and high (e.g., greater than 84% range) arterial oxygen saturation values are more accurately calculated. In one embodiment, light emitted from a near 660 nm and a near 900 nm emitter pair may be used when the arterial oxygen saturation range is high. In another embodiment, light emitted from a near 730 nm and a near 900 nm emitter pair may be used when the arterial oxygen saturation range is low. In yet another embodiment, light emitted from both a near 660 nm-900 nm emitter pair and light emitted from a near 730 nm-900 nm emitter pair may be used when the arterial oxygen saturation range is in the middle range. Priming techniques may also be used to reduce or eliminate start up delays of certain oximetry system components.

23 Claims, 9 Drawing Sheets

(56) References Cited

U.S. PATENT DOCUMENTS

| | | | |
|---|---|---|---|
| 5,299,570 | A | 4/1994 | Hatschek |
| 5,361,758 | A | 11/1994 | Hall et al. |
| 5,385,143 | A | 1/1995 | Aoyagi |
| 5,413,100 | A | 5/1995 | Barthelemy et al. |
| 5,494,032 | A | 2/1996 | Robinson et al. |
| 5,497,769 | A | 3/1996 | Gratton et al. |
| 5,522,388 | A | 6/1996 | Ishikawa et al. |
| 5,524,617 | A | 6/1996 | Mannheimer |
| 5,582,169 | A | 12/1996 | Oda et al. |
| 5,596,986 | A | 1/1997 | Goldfarb |
| 5,632,273 | A | 5/1997 | Suzuki |
| 5,746,206 | A | 5/1998 | Mannheimer |
| 5,774,213 | A | 6/1998 | Trebino et al. |
| 5,782,237 | A * | 7/1998 | Casciani et al. .............. 600/476 |
| 5,782,756 | A | 7/1998 | Mannheimer |
| 5,817,008 | A | 10/1998 | Rafert et al. |
| 5,842,979 | A | 12/1998 | Jarman |
| 5,983,122 | A | 11/1999 | Jarman |
| 6,026,314 | A | 2/2000 | Amerov et al. |
| 6,064,899 | A | 5/2000 | Fein et al. |
| 6,078,833 | A | 6/2000 | Hueber |
| 6,104,938 | A | 8/2000 | Huiku et al. |
| 6,213,952 | B1 | 4/2001 | Finarov et al. |
| 6,230,035 | B1 | 5/2001 | Aoyagi et al. |
| 6,272,363 | B1 | 8/2001 | Casciani et al. |
| 6,343,223 | B1 | 1/2002 | Chin et al. |
| 6,400,971 | B1 | 6/2002 | Finarov et al. |
| 6,430,513 | B1 | 8/2002 | Wang et al. |
| 6,438,399 | B1 | 8/2002 | Kurth |
| 6,456,862 | B2 | 9/2002 | Benni |
| 6,526,301 | B2 | 2/2003 | Larsen et al. |
| 6,587,703 | B2 | 7/2003 | Cheng et al. |
| 6,594,513 | B1 | 7/2003 | Jobsis et al. |
| 6,597,931 | B1 | 7/2003 | Cheng et al. |
| 6,654,622 | B1 | 11/2003 | Eberhard et al. |
| 6,662,033 | B2 | 12/2003 | Casciani et al. |
| 6,671,526 | B1 | 12/2003 | Aoyagi et al. |
| 6,714,805 | B2 | 3/2004 | Jeon et al. |
| 6,731,963 | B2 | 5/2004 | Finarov et al. |
| 6,801,799 | B2 | 10/2004 | Mendelson |
| 6,842,635 | B1 | 1/2005 | Parker |
| 6,873,865 | B2 | 3/2005 | Steuer et al. |
| 6,961,598 | B2 | 11/2005 | Diab |
| 6,983,178 | B2 | 1/2006 | Fine et al. |
| 7,027,849 | B2 | 4/2006 | Al-Ali |
| 7,047,055 | B2 | 5/2006 | Boas et al. |
| 7,072,701 | B2 | 7/2006 | Chen et al. |
| 7,133,711 | B2 | 11/2006 | Chernoguz et al. |
| 7,209,775 | B2 | 4/2007 | Bae et al. |
| 7,221,970 | B2 | 5/2007 | Parker |
| 7,236,813 | B2 | 6/2007 | Parker |
| 7,283,242 | B2 | 10/2007 | Thornton |
| 7,319,894 | B2 | 1/2008 | Higgins |
| 7,343,186 | B2 | 3/2008 | Lamego |
| 7,400,918 | B2 | 7/2008 | Parker et al. |
| 2002/0042558 | A1 | 4/2002 | Mendelson |
| 2002/0128544 | A1 | 9/2002 | Diab et al. |
| 2002/0173706 | A1 | 11/2002 | Takatani |
| 2002/0173709 | A1 | 11/2002 | Fine et al. |
| 2003/0144584 | A1 | 7/2003 | Mendelson |
| 2003/0236452 | A1 | 12/2003 | Melker et al. |
| 2004/0024297 | A1 | 2/2004 | Chen et al. |
| 2004/0107065 | A1 | 6/2004 | Al-Ali |
| 2004/0116788 | A1 | 6/2004 | Chernoguz et al. |
| 2004/0116789 | A1 | 6/2004 | Boas et al. |
| 2005/0070773 | A1 | 3/2005 | Chin et al. |
| 2005/0131286 | A1 | 6/2005 | Parker et al. |
| 2006/0030764 | A1 | 2/2006 | Porges et al. |
| 2006/0052680 | A1 | 3/2006 | Diab |
| 2006/0189861 | A1 | 8/2006 | Chen et al. |
| 2006/0211923 | A1 | 9/2006 | Al-Ali et al. |
| 2006/0211924 | A1 | 9/2006 | Dalke et al. |
| 2006/0211932 | A1 | 9/2006 | Al-Ali et al. |
| 2006/0241363 | A1 | 10/2006 | Al-Ali et al. |
| 2007/0060809 | A1 | 3/2007 | Higgins |
| 2007/0078311 | A1 | 4/2007 | Al-Ali et al. |
| 2007/0129616 | A1 | 6/2007 | Rantala |
| 2007/0282178 | A1 | 12/2007 | Scholler et al. |
| 2007/0282183 | A1 | 12/2007 | Scholler et al. |
| 2008/0004513 | A1 | 1/2008 | Walker et al. |
| 2008/0081972 | A1 | 4/2008 | Debreczeny |
| 2008/0108887 | A1 | 5/2008 | Higgins |
| 2008/0132771 | A1 | 6/2008 | Parker et al. |
| 2008/0139906 | A1 | 6/2008 | Bussek |
| 2008/0139908 | A1 | 6/2008 | Kurth |
| 2008/0154104 | A1 | 6/2008 | Lamego et al. |
| 2008/0171926 | A1 | 7/2008 | Sola I Caros et al. |
| 2008/0208019 | A1 | 8/2008 | Nitzan |
| 2008/0214911 | A1 | 9/2008 | Forstner |
| 2008/0221414 | A1 | 9/2008 | Baker |
| 2008/0221464 | A1 | 9/2008 | Al-Ali |
| 2008/0234560 | A1 | 9/2008 | Nomoto et al. |
| 2008/0242958 | A1 | 10/2008 | Al-Ali et al. |
| 2008/0300473 | A1 | 12/2008 | Benni |

FOREIGN PATENT DOCUMENTS

| | | |
|---|---|---|
| EP | 0430340 | 6/1991 |
| EP | 0793942 | 9/1997 |
| EP | 01491135 | 12/2004 |
| JP | 63275325 | 11/1988 |
| JP | 3245042 | 10/1991 |
| JP | 5049625 | 3/1993 |
| JP | 5212016 | 8/1993 |
| JP | 11019074 | 1/1999 |
| JP | 11244268 | 9/1999 |
| JP | 2003194714 | 7/2003 |
| JP | 20048572 | 1/2004 |
| JP | 2004148069 | 5/2004 |
| JP | 2004148070 | 5/2004 |
| JP | 2004159810 | 6/2004 |
| JP | 2004248820 | 9/2004 |
| JP | 2004329928 | 11/2004 |
| JP | 3635331 | 4/2005 |
| JP | 200595581 | 4/2005 |
| JP | 2005169020 | 6/2005 |
| JP | 2005278758 | 10/2005 |
| JP | 2006075354 | 3/2006 |
| JP | 2006122693 | 5/2006 |
| JP | 3797454 | 7/2006 |
| JP | 2006239267 | 9/2006 |
| JP | 2007167183 | 7/2007 |
| JP | 2007196001 | 8/2007 |
| JP | 2007259918 | 10/2007 |
| JP | 2008194488 | 8/2008 |
| WO | WO9101678 | 2/1991 |
| WO | WO9316629 | 9/1993 |
| WO | WO9403102 | 2/1994 |
| WO | WO9749330 | 12/1997 |
| WO | WO9947039 | 9/1999 |
| WO | WO03071939 | 9/2003 |
| WO | WO03077750 | 9/2003 |
| WO | WO2005007215 | 1/2005 |
| WO | WO2005025399 | 3/2005 |
| WO | WO2005099568 | 10/2005 |
| WO | WO2006124696 | 11/2006 |
| WO | WO2007097702 | 8/2007 |
| WO | WO2008039187 | 4/2008 |
| WO | WO2008134813 | 11/2008 |

OTHER PUBLICATIONS

Mannheimer, P.D., et al.; "Physio-optical consideration in the design of fetal pulse oximetry sensors," *European Journal of Obstetrics & Gynecology and Reproductive Biology*, 72 Suppl. 1, 1997, p. S9-S19.

Lutter, N., et al.; "Comparison of Different Evaluation Methods for a Multi-wavelength Pulse Oximeter," *Biomedizinische Technik*, vol. 43, (1998).

Aoyagi, T., et al.; "Pulse Oximeters: background, present and future," *Neonatal Care*, vol. 13, No. 7, pp. 21-27 (2000) (Article in Japanese—contains English summary of article).

(56) References Cited

OTHER PUBLICATIONS

Yoon, Gilwon, et al.; Multiple diagnosis based on Photoplethysmography: hematocrit, SpO2, pulse and respiration, Optics in Health Care and Biomedical optics: Diagnostics and Treatment; *Proceedings of the SPIE*, vol. 4916; pp. 185-188 (2002).

Ericson, M.N., et al.; "In vivo application of a minimally invasive oximetry based perfusion sensor," *Proceedings of the Second Joint EMBS/BMES Conference*, Houston, Texas; Oct. 23-26, 2002, p. 1789-1790.

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, p. 1777-1778.

Mannheimer, Paul D.; "Design and Validation of Pulse Oximetry for Low Saturation", Anesth Analg 2002:94-521-525.

\* cited by examiner

| SpO₂ LEVEL | WEIGHTFACTOR$_{660}$ | WEIGHTFACTOR$_{770}$ |
|---|---|---|
| 89 | 0.95 | 0.05 |
| 88 | 0.90 | 0.10 |
| 87 | 0.85 | 0.15 |
| 86 | 0.80 | 0.20 |
| 85 | 0.75 | 0.25 |
| 84 | 0.70 | 0.30 |
| 83 | 0.65 | 0.35 |
| 82 | 0.60 | 0.40 |
| 81 | 0.55 | 0.45 |
| 80 | 0.50 | 0.50 |
| 79 | 0.45 | 0.55 |
| 78 | 0.40 | 0.60 |
| 77 | 0.35 | 0.65 |
| 76 | 0.30 | 0.70 |
| 75 | 0.25 | 0.75 |
| 74 | 0.20 | 0.80 |
| 73 | 0.15 | 0.85 |
| 72 | 0.10 | 0.90 |
| 71 | 0.05 | 0.95 |

⇒ TRANSITION SpO₂

WAVELENGTH SWITCHING FOR PULSE OXIMETRY

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The present disclosure relates generally to medical devices and, more particularly, to sensors used for sensing physiological parameters of a patient. In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin ($SpO_2$) in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms. This determination may be performed in a monitor coupled to the sensor that receives the necessary data for the blood constituent calculation.

Conventional two wavelength pulse oximeters emit light from two light emitting diodes (LEDs) into a pulsatile tissue bed and collect the transmitted light with a photodiode positioned on an opposite surface (transmission pulse oximetry) or on an adjacent surface (reflectance pulse oximetry). The LEDs and photodetector are housed in a reusable or disposable sensor which communicates with the pulse oximeter. For estimating oxygen saturation, at least one of the two LEDs' primary wavelengths is typically chosen at some point in the electromagnetic spectrum where the absorption of oxyhemoglobin ($HbO_2$) differs from the absorption of reduced hemoglobin (Hb). The second of the two LEDs' wavelength is typically at a different point in the spectrum where, additionally, the absorption differences between Hb and $HbO_2$ are different from those at the first wavelength.

The first LED is typically configured to emit light with a wavelength in the near red portion of the visible spectrum 660 nanometers (nm) and the second LED is configured to emit light with a wavelength in the near infrared portion of the spectrum near 900 nm. The near 660 nm-900 nm wavelength pair has been selected because it provides for the best accuracy when $SpO_2$ is high (e.g., in the 85% and above range). Some pulse oximeters replace the near 660 nm LED with an LED configured to emit light in the far red portion of the spectrum near 730 nm. The near 730 nm-900 nm wavelength pair has been selected because it provides for the best accuracy when $SpO_2$ is low (e.g., in the range below 75%). Unfortunately, inaccuracies result from using a single wavelength pair. The single pair of wavelengths can only properly account for a portion of the entire arterial oxygen saturation range.

SUMMARY

Certain aspects commensurate in scope with the disclosed embodiments are set forth below. It should be understood that these aspects are presented merely to provide the reader with a brief summary of certain embodiments and that these aspects are not intended to limit the scope of the disclosure. Indeed, the disclosure and/or claims may encompass a variety of aspects that may not be set forth below.

The present techniques may provide for more accurate estimates of arterial oxygen saturation using pulse oximetry by switching between a wavelength spectrum of at least a first and a second light source so that the arterial oxygen saturation estimates at low, medium, and high arterial oxygen saturation values are more accurately measured. Indeed, the techniques disclosed herein may allow for an increased accuracy in measurement of arterial oxygen saturation across a wider range of saturation levels. The techniques may be applicable to both reflectance and transmission pulse oximetry.

In a first example, the disclosed techniques may be particularly useful for estimating arterial oxygen saturation of a fetus during labor where the saturation range of principal importance and interest is generally between 15% and 65%. As another example, these techniques may be particularly useful for estimating arterial saturation of a cardiac patient who experiences significant shunting of venous blood into the arteries in their heart and whose saturation range of principle importance and interest is roughly between 50% and 80%. The disclosed techniques may facilitate improved $SpO_2$ accuracy over all levels of arterial oxygen saturation and can be used on a host of different patient classes including fetuses, neonates, cardiac patients, children, and adults.

One embodiment includes a sensor with at least three LEDs which may be configured to emit light at wavelengths near 660 nm, near 730 nm, and near 900 nm, for example. It is to be understood that the LEDs will emit light at a wavelength range due to small defects in manufacture, environmental conditions, etc. The wavelengths near 660 nm and 900 nm may be selected for calculations at higher arterial oxygen saturations and the wavelengths near 730 nm and 900 nm may be selected for calculations at lower arterial oxygen saturations.

The sensor's LED configuration may permit the use of two light emitter pairs, one pair set to emit light at near 660 nm and 900 nm and a second pair set to emit light at near 730 nm and 900 nm, where the same 900 nm LED may be used in each pair. Light from the 730 nm-900 nm emitter pair may then be used to calculate the $SpO_2$ when the arterial oxygen saturation is low (e.g., below 75%) and light from the 660 nm-900 nm emitter pair may then be used to calculate the $SpO_2$ when the arterial oxygen saturation is high (e.g., greater than 84%). Further, light from both emitter pairs may be used to calculate the $SpO_2$ in the region where the arterial oxygen saturation is greater than or equal to 75% and less than or equal to 84%, heretofore referred to as the "transition region." The transition region is so named because it is in the range in which the patient's $SpO_2$ value is transitioning from the high range to the low range or vice versa.

The calculation of the transition range $SpO_2$ when using two light emitter pairs may involve any of several techniques. In one embodiment, the system may arbitrate between the $SpO_2$ values calculated using the light from the two light emitter pairs and choose one to use in making the final $SpO_2$ calculation. In another embodiment, the system may calculate two $SpO_2$ values, one value corresponding to each one of the two light emitter pairs, and then calculate the average of the two $SpO_2$ values. In yet another embodiment, the system may use a table of weight factors and a weight-averaging equation to combine the $SpO_2$ values derived from the two light emitter pairs. It is to be noted that the weight factors may be linear or non-linear and may be derived from a lookup table or an equation.

In one embodiment, the sensor cable may be connected to the monitor and the sensor may be configured to accept light drive signals from the monitor. The sensor may use the light drive signals to select which LED(s) to turn on and which LED(s) to turn off. In another embodiment, the sensor cable may contain a multiplexer. The multiplexer may be configured to accept light drive signals from the monitor and to use the light drive signals to select which LED(s) to turn on and which LED(s) to turn off. The use of a multiplexer may be advantageous because the multiplexer may allow the monitor to be connected to different types of sensors.

In another embodiment, hardware and software components in both the sensor and the monitor may be primed as the $SpO_2$ measurement approaches the transition range so as to reduce a startup time of the components. The priming allows for the components to more quickly acquire measurements as the arterial oxygen level enters into the transition region. Indeed, priming may allow for a much improved accuracy and quality of measurements in the transition region.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain embodiments, at least three LEDs may be used so as to enable the measurement of $SpO_2$ through a broader spectrum of light. Such measurements may then be combined by using techniques described in more detail below to arrive at a more precise $SpO_2$ measurement. The $SpO_2$ measurement may be considerably improved, particularly in arterial oxygen ranges (e.g., transition region) where the $SpO_2$ measurement may be transitioning from a low arterial oxygen range to a high arterial oxygen range, or vice versa. In one example, one of the at least three LEDs may be driven in arterial oxygen ranges in close proximity to the transition range (e.g., within 5%) so as to aid in priming hardware and software components of a pulse oximeter system. The priming enables the pulse oximeter to acquire data by using all three LEDs almost immediately when the arterial range enters the transition region. Such capability increases the accuracy of the $SpO_2$ measurement in the transition region. In another example, all three of the LEDs may be used all of the time. In this example, using all the LEDs may thus further remove the time spent priming, and may also increase the amount of data used for deriving measurements of interest.

Figure 1:
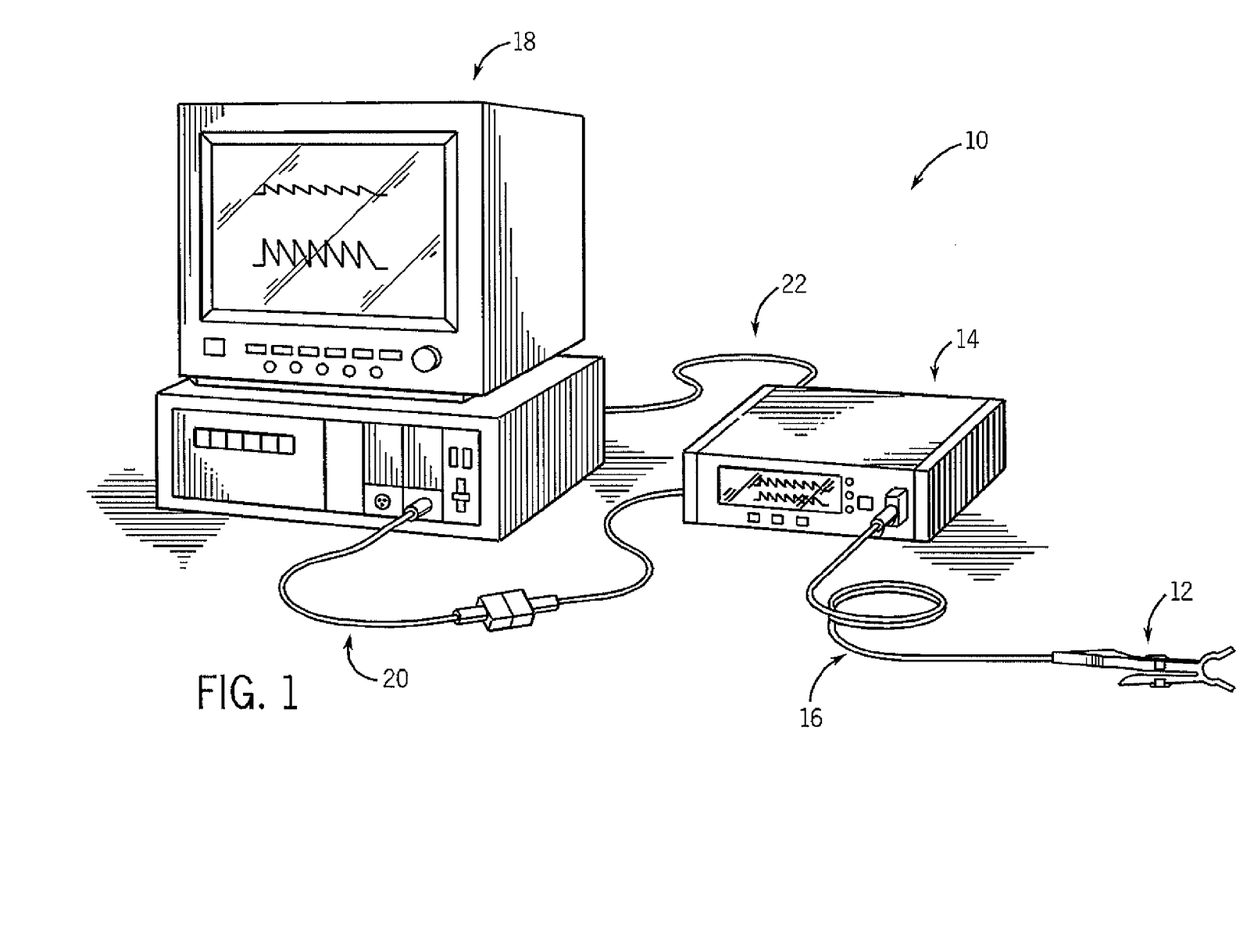
FIG. 1 depicts a diagram of an embodiment of a pulse oximetry system.

FIG. 1 depicts a medical device, such as a pulse oximeter system 10. The sensor 12 may be coupled to the monitor 14 via sensor cable 16. The monitor 14 may be any suitable pulse oximeter, such as those available from Nellcor Puritan Bennett, LLC. Furthermore, to upgrade conventional operation provided by the monitor 14 to provide additional functions, monitor 14 may be coupled to a multi-parameter patient monitor 18 via a cable 20 connected to a sensor input port or via a cable 22 connected to a digital communication port, for example.

Figure 2:
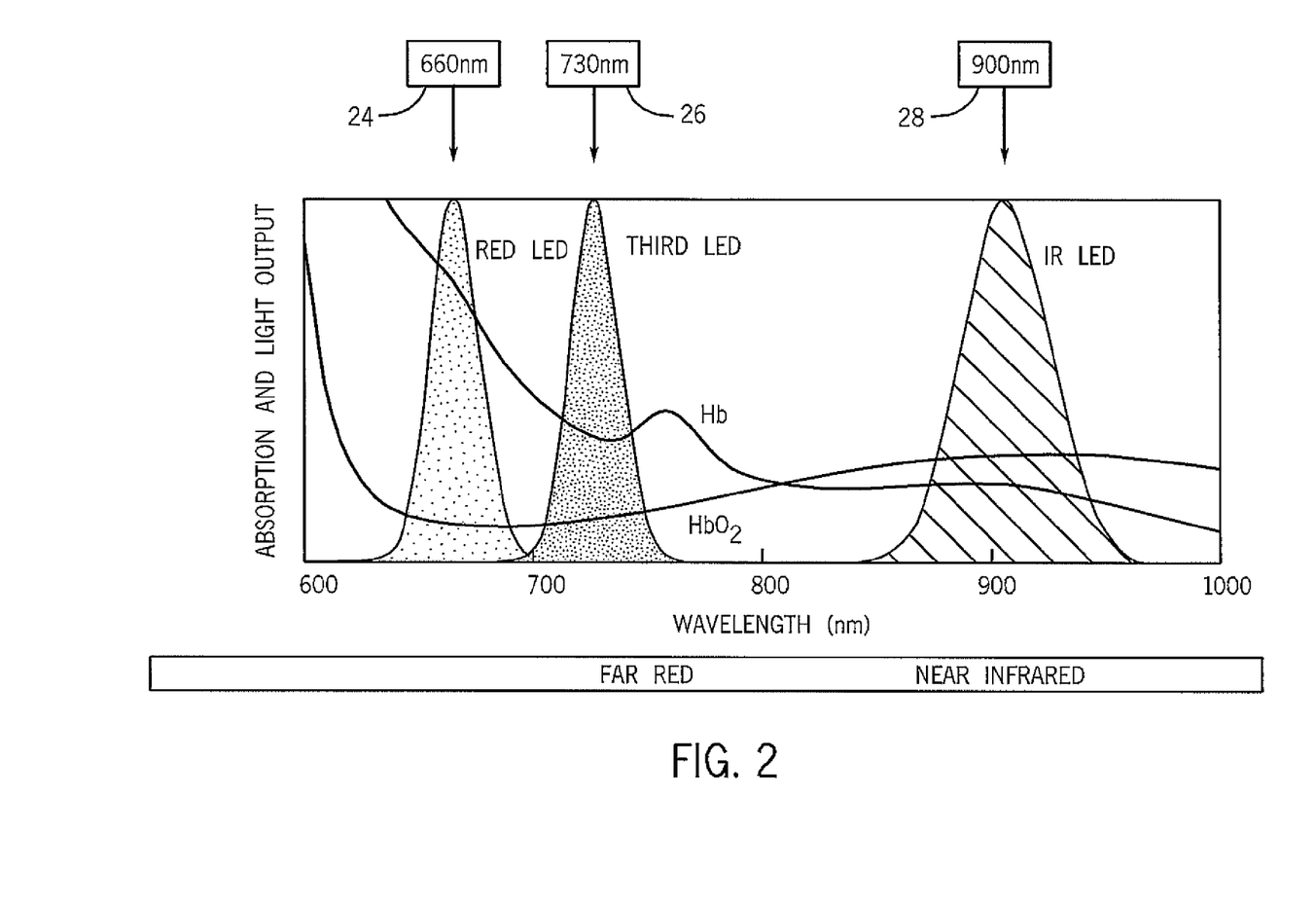
FIG. 2 illustrates a chart of the absorption characteristics of oxyhemoglobin ($HbO_2$) and reduced hemoglobin (Hb) versus wavelength showing absorption in the red and infrared LED wavelengths.

FIG. 2 depicts a chart of the absorption characteristics of oxyhemoglobin ($HbO_2$) and reduced hemoglobin (Hb). Three wavelength ranges include the far red wavelengths at approximately 620-700 nm; the far red wavelengths at approximately 690-770 nm; and the infrared wavelengths at approximately 860-940 nm. Light within each one of the three wavelength ranges may be respectively emitted by a 660 nm emitter 24, a 730 nm emitter 26, and a 900 nm emitter 28, for example. A 660 nm emitter 24 emits a wavelength of light that has a relatively high Hb absorption coefficient but a relatively low $HbO_2$ absorption coefficient. A 900 nm emitter 28 emits a wavelength of light that has different absorption coefficients for Hb and $HbO_2$ from the light emitted by the 660 nm emitter. This difference may be used to derive a $SpO_2$ measurement by analyzing the light emitted by a 660 nm emitter 24 and by a 900 nm emitter 28. A second $SpO_2$ measurement may also be derived by analyzing the light emitted by a 730 nm 26 and by a 900 nm emitter 28.

The $SpO_2$ measurement derived by using the light from a 660 nm-900 nm emitter pair may be utilized for arterial oxygen saturation ranges in a high range. However, when arterial oxygen saturation is in a low range, the $SpO_2$ measurement derived by using light from a 660 nm-900 nm emitter pair may become less accurate. Better accuracy at the arterial oxygen saturation low range may be achieved by using a 730 nm emitter 26 instead of the 660 mm emitter 24. Therefore, more precise estimates of arterial oxygen saturation using pulse oximetry may be achieved by switching between different emitters so that the wavelengths that result in the most accurate $SpO_2$ determination are emitted.

Figure 3A:
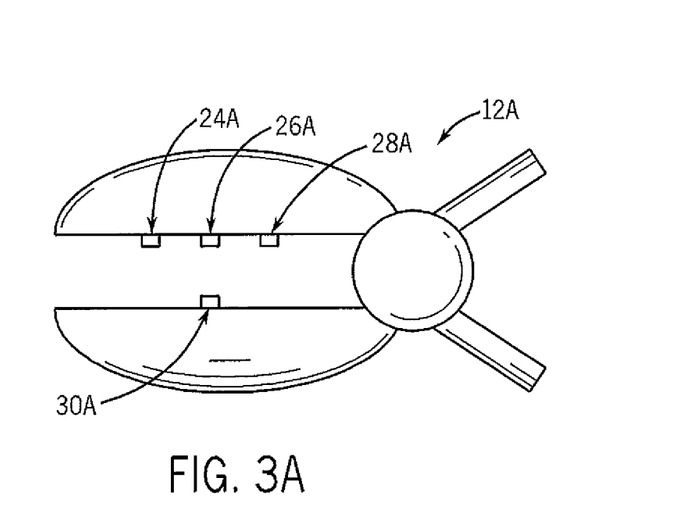
FIG. 3A depicts a drawing of a sensor having three LEDs with a photodetector positioned to receive the LED signals in a transmission mode of operation.
Figure 3B:
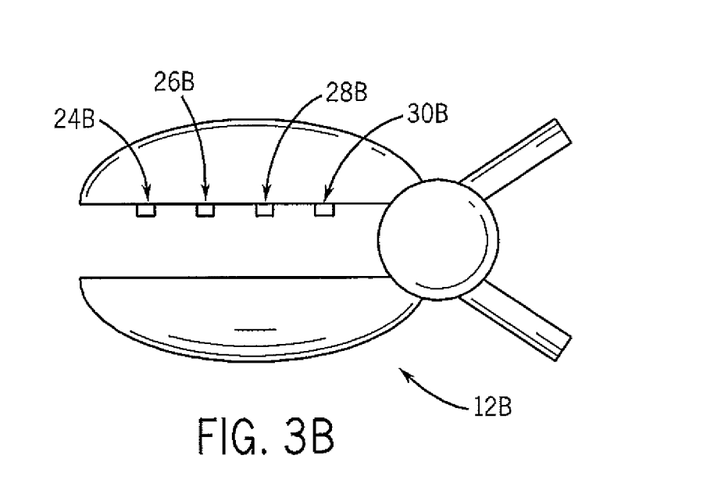
FIG. 3B depicts a drawing of a sensor having three LEDs with a photodetector positioned to receive the LED signals in a reflectance mode of operation.

Turning to FIG. 3A, the figure illustrates a transmission type sensor 12A wherein light from the 660 nm emitter 24A, light from the 730 nm emitter 26A, and light from the 900 nm emitter 28A passes through one side of a vascularized tissue to reach a detector 30A on the other side of the tissue. FIG. 3B depicts a reflectance type sensor 12B wherein the 660 nm emitter 24B, the 730 nm 26B, the 900 nm emitter 28B, and the detector 30B are all positioned on the same side of the sensor 12B so that the emitted light is reflected through the vascularized tissue underneath the emitters back into the detector 30B. Light from the 660 nm emitter 24 and the 900 nm emitter 28 may be selected to give more accurate estimates of arterial oxygen saturation in the high saturation range, for example. Light from the 730 nm emitter 26 and the 900 nm emitter 28 may be selected to give more accurate estimates of arterial oxygen saturation in the low saturation range, for example. Further, light from the 660 nm emitter 24 and the 900 nm emitter 28 pair and light from the 730 nm emitter 26 and the 900 nm emitter 28 pair may be used to calculate the $SpO_2$ in the transition region where the arterial oxygen saturation is in a transition range (i.e., between the low and the high arterial saturation ranges). It should be noted that the spacing of the emitters and the detectors of FIGS. 3A and 3B are for illustrative purposes and not to scale. Indeed, the same light path length for all emitter-detector pairs is usually preferred, and accordingly, the LEDs may be positioned in close proximity to each other.

Figure 4:
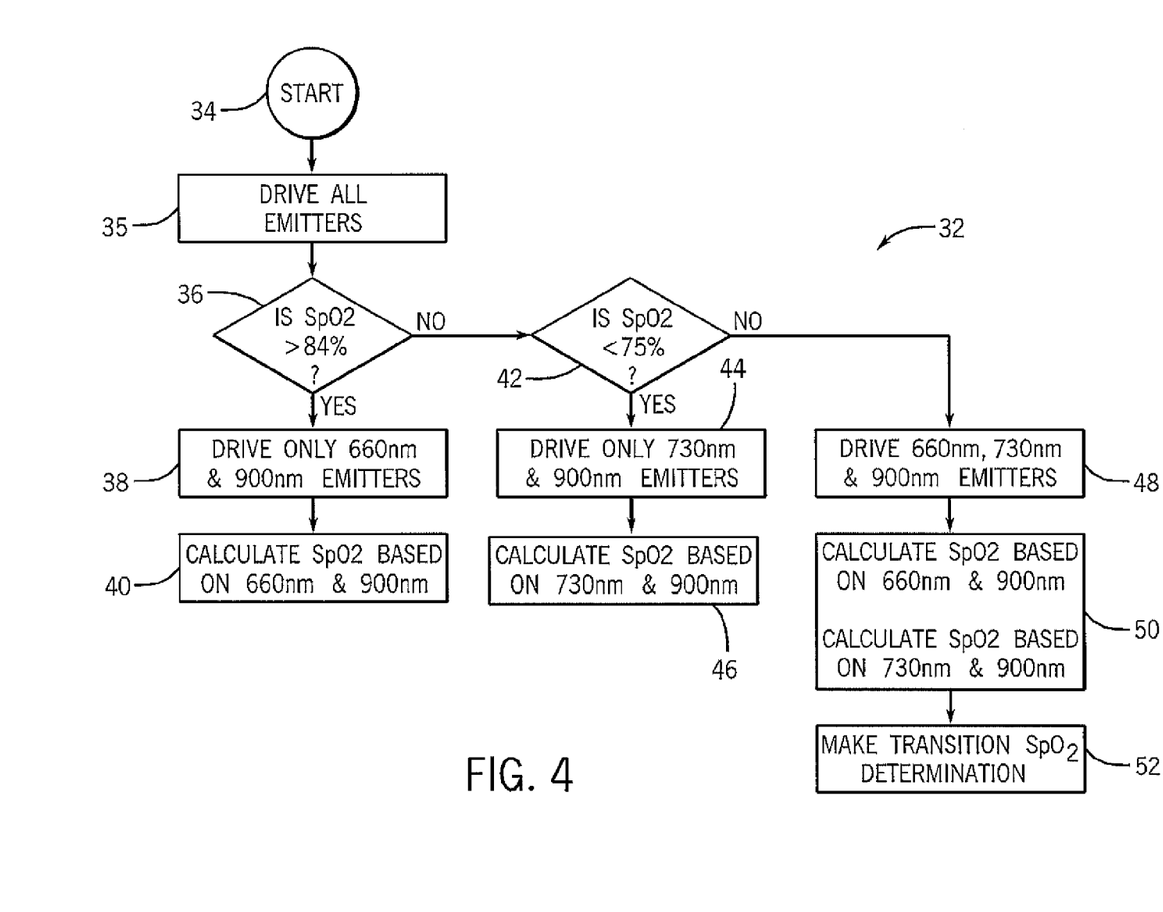
FIG. 4 illustrates a flow diagram of a method of selectively switching between at least two wavelengths, e.g., near 660 nm and near 730 nm, in a sensor, such as those illustrated in FIG. 1, FIG. 2A and FIG. 2B.

Turning to FIG. 4, flow diagram 32 shows one embodiment of the switching methodology that may used to determine which emitters will be driven to emit light. In the depicted example, a system start (step 34) may begin by driving all of the emitters (e.g., 660 nm emitter 24, 730 nm emitter 26, and 900 nm emitter 28) (step 35). In certain examples, a more accurate initial estimate of the arterial oxygen saturation may be arrived at by initializing the system with all three emitters 24, 26, and 28. In one example, all three emitters may be used to calculate the arterial oxygen saturation. In another example, only two of the emitters may be used after system start (step 34). For example, the 660 nm-900 nm emitter pair or the 730 nm-900 nm emitter pair may be driven after system start (step 34) and used to measure the arterial oxygen saturation.

The previously calculated $SpO_2$ value is considered and a determination is made in step 36 to determine if the $SpO_2$ value is greater than 84%. If the $SpO_2$ value is greater than 84%, then only the 660 nm emitter 24 and the 900 nm 26 emitter are driven to emit light (step 38). The detector signals resulting from the use of the 660 nm emitter 24 and the 900 nm emitter 26 are then processed at step 40 to calculate the next $SpO_2$ value. The 660 nm-900 nm emitter pair is selected to emit light when the previously calculated $SpO_2$ value is greater than 84% because when blood perfused tissue has a high arterial oxygen saturation value (e.g., greater than 84%), then the $SpO_2$ value may be more accurately calculated by using light with a wavelength near 660 nm and light with a wavelength near 900 nm.

If the previously calculated $SpO_2$ value is not greater than 84%, then a determination is made at step 42 to determine if the $SpO_2$ value is less than 75%. If the previously calculated $SpO_2$ value is less than 75%, then only the 730 nm emitter 26 and the 900 nm emitter 28 are driven to emit light (step 44). The detector 30 signals resulting from the use of the 730 nm emitter and the 900 nm emitter are then processed at step 46 to calculate the next $SpO_2$ value. The 730 nm-900 nm emitter pair is selected when the previously calculated $SpO_2$ value is less than 75% because when blood perfused tissue has a low arterial oxygen saturation value (e.g., less than 75%), then the $SpO_2$ value may be more accurately measured by using light with a wavelength near 730 nm and light with a wavelength near 900 nm. It is to be understood that the values of 84% and 75% may be approximate. That is in other embodiments, values slightly larger or smaller may be used, for example, values approximately near ±7% of the illustrated values.

If the previously calculated $SpO_2$ value is not greater than 84% and not less than 75%, then the 660 nm emitter 24, the 730 nm emitter 26, and the 900 nm emitter 28 are driven to emit light (step 48). One $SpO_2$ value is calculated in step 50 based on the detector 30 signals resulting from the use of the 660 nm emitter 24 and the 900 nm emitter 28, and a second $SpO_2$ value is calculated in step 50 based on the detector 30 signals resulting from the use of the 730 nm emitter 26 and the 900 nm emitter 28. Both of the $SpO_2$ values calculated in step 50 are then processed in step 52 to arrive at the next $SpO_2$ value determination. The $SpO_2$ value determined at step 52 is heretofore referred to as the "Transition $SpO_2$ Value", because the value is inside the transition range where the arterial oxygen saturation is transitioning between high and low values (e.g., greater than or equal to 75% and less than or equal to 84%).

When a $SpO_2$ value is in the transition range (e.g., when the arterial oxygen saturation is greater than or equal to 75% and less than or equal to 84%), two $SpO_2$ values are calculated (see step 50 of FIG. 4). One value is referred to as $SpO2_{660}$ and corresponds to the 660 nm-900 nm emitter pair, and a second value is referred to as $SpO2_{730}$ and corresponds to the 730 nm-900 nm emitter pair. In this example flow diagram 32, a single transition $SpO_2$ value is determined based on these two calculations, and this determination may be made in any suitable manner. Additionally, a direct calculation may be made involving all three wavelengths, 660 nm, 730 nm, and 900 nm.

Figure 5:
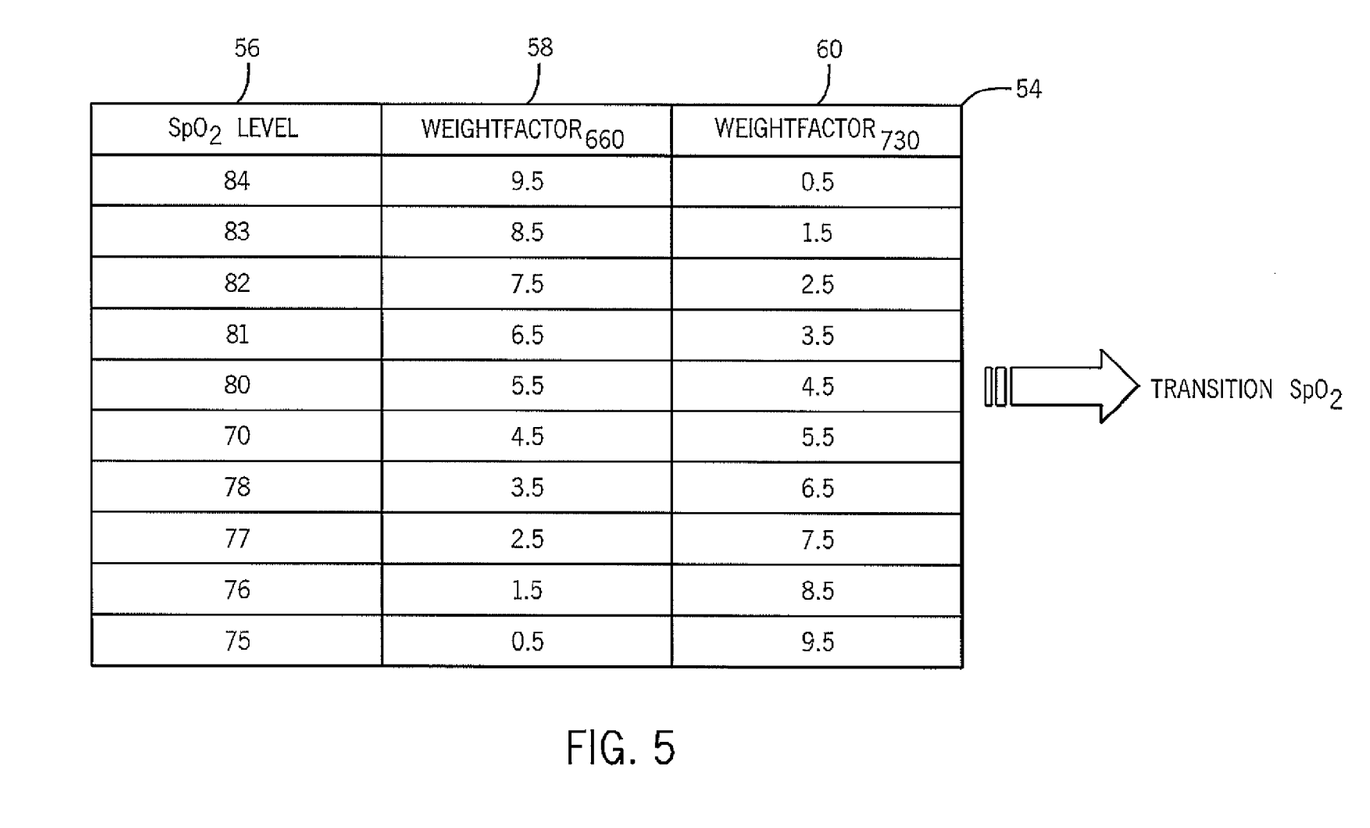
FIG. 5 illustrates a table showing an example of different weight factors and $SpO_2$ levels that may be utilized to calculate the $SpO_2$ for a transition range of operation such as those in FIG. 4.

In one example, FIG. 5 depicts a table 54 of weight factors that may be used, for example, by the methodology described in FIG. 4, to determine the transition $SpO_2$ value. To determine the transition $Sp_{O2}$ value under this embodiment, the $SpO2_{660}$ value associated with the 660 nm-900 nm emitter pair is first chosen from one of the cells in column 56 ($SpO_2$ Level) of table 54 and the associated $WeightFactor_{660}$ cell value in column 58 of table 54 is selected. The $SpO2_{730}$ value associated with the 730 nm-900 nm emitter pair is also chosen from one of the cells in column 56 ($SpO_2$ Level) of table 54 and the associated $WeightFactor_{730}$ cell value in column 60 of table 54 is selected. The following equation may then be used to arrive at the transition $SpO_2$ value:

$$\text{Transition } SpO_2 = \frac{\left(\left(SpO2_{660} \times \frac{WeightFactor_{660}}{10}\right) + \left(SpO2_{730} \times \frac{WeightFactor_{730}}{10}\right)\right)}{\left(\frac{WeightFactor_{660} + WeightFactor_{730}}{10}\right)} \quad (1)$$

It is to be understood that other linear and/or non-linear equations and weight factors may be used. For example, another equation may have the $WeightFactor_{660}$ and the $WeightFactor_{7300}$ normalized between 0 and 1.0 instead of between 0 and 10.

The use of the example weight factor table 54 and the weight factor equation (1) may allow for increased accuracy in the transition range because more weight may be given to the $SpO_2$ value of the emitter pair that is closest to its most accurate usage range. For example, the $SpO2_{660}$ value derived from the use of the emitter pair 660 nm-900 nm may be given more weight when the last calculated $SpO_2$ value in the transition range is closer to 84%. Similarly, the $SpO2_{730}$ value derived from the use of the 730 nm-900 nm emitter pair may be given more weight when the last calculated $SpO_2$ value in the transition range is closer to 75%. It is to be understood that other weighing embodiments may be used, for example, logarithmic weighing, Gaussian weighing, and empirical weighing.

Logarithmic weighing would replace the weight factor values of table 54 and the weight factor equation with weight factors and a weight equation that may result more weight being given to the various $SpO_2$ values based on the logarithmic scale that was chosen. Gaussian weighing would replace the weight factor values of table 54 and the weight factor equation with weight factors and a weight equation that may result in more weight be given to the $SpO_2$ values based on the Gaussian scale that was chosen. Empirical weighing would replace the weight factor values of table 54 and the weight factor equation with weight factors and a weight equation derived from empirical studies of patient tissue. It is also to be noted that the table 54 could be replaced with an equation. For example, an equation such as $WeightFactor_{660}=w=(SPO_2Level-75)/10+0.05$, and $WeightFactor_{730}=1-w$ when the $SPO_2$ level is between 75% and 84% may be used. When the $SPO_2$ level is less than 75%, $w=0$. When the $SPO_2$ level is greater than 84%, $w=1.0$. Other suitable equations may be used, including equations incorporating logarithmic and/or exponential functions. In another embodiment, the $SpO2_{660}$ value associated with the 660 nm-900 nm emitter pair, and the $SpO2_{730}$ value associated with the 730 nm-900 nm emitter pair may be averaged to determine the transition $SpO_2$ value.

In another example, the $SpO2_{660}$ value associated with the 660 nm-900 nm emitter pair, and the $SpO2_{730}$ value associated with the 730 nm-900 nm emitter pair may be arbitrated to determine the transition $SpO_2$ value. The arbitration algorithm may, for example, select the value of either $SpO2_{660}$ or $SpO2_{730}$ as the final transition value, based on which one gives a higher or lower value, selecting $SpO2_{660}$ or $SpO2_{730}$ based on a lookup table, which is closest to the previous value, among others. Arbitrating between the $SpO2_{660}$ and the $SpO2_{730}$ values may be advantageous because this technique may give preference to the $SpO2_{660}$ or to the $SpO2_{730}$ values based on certain arbitration decisions such as higher accuracy of one value at certain transition $SpO_2$ subranges. It is to be understood that certain embodiments, including the arbitration algorithm example, may include algorithms suitable for calculating a smooth transition band or curve when transitioning between using a different emitter pair or calculation. Smooth transitioning may eliminate fluctuations in the displayed measurement not corresponding to actual physical changes.

Figure 6:
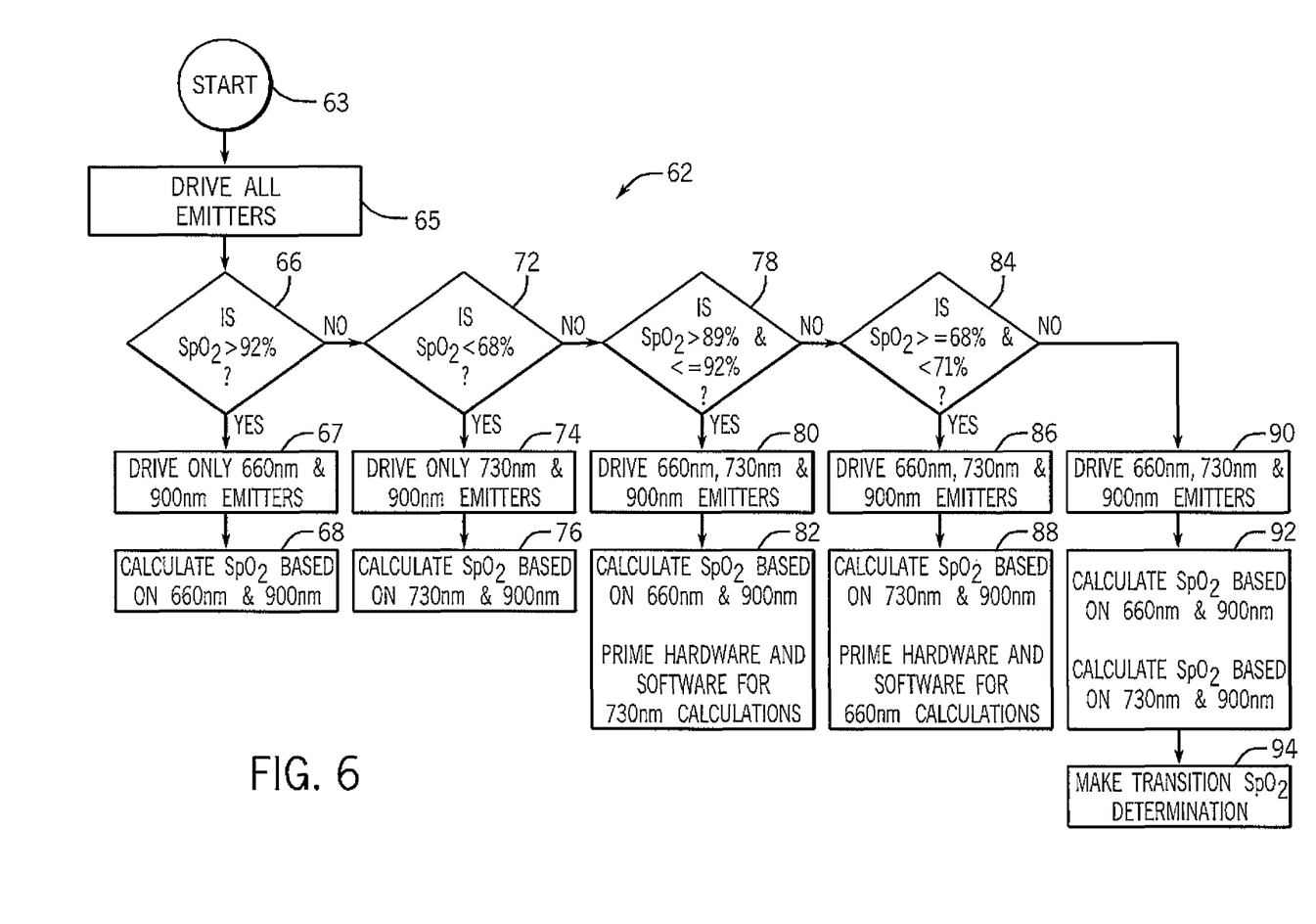
FIG. 6 illustrates a flow diagram of another method of selectively switching between at least two wavelengths, e.g., near 660 nm and near 730 nm, in a sensor, such as those illustrated in FIG. 1, FIG. 2A and FIG. 2B.

Turning to FIG. 6, a flow diagram 62 shows a second embodiment of the switching methodology that may used to determine which emitters will be driven to emit light. In his embodiment, a priming technique is also used so as to enable the pulse oximeter to acquire data from all three LEDs almost immediately upon the arterial range entering the transition region. Further, the transition region in this embodiment may be a slightly broader transition region when compared to the transition region example described above with respect to FIGS. 4 and 5. A slightly broader transition region may improve the measurement quality by enabling an increase in measurements using all three LEDs. Indeed, such capabilities allow for increased accuracy, particularly in measuring arterial oxygen saturation in the transition region.

In the depicted example, a system start (step 63) may begin driving all of the emitters (e.g., 660 nm emitter 24, 730 nm emitter 26, and 900 nm emitter 28) (step 65). In this example, a more accurate initial estimate of the arterial oxygen saturation may be arrived at by initializing the system with all three emitters 24, 26, and 28 (step 65). In one example, all three emitter may be used to calculate the arterial oxygen saturation. In another example, only two of the emitters may be used after system start (step 63). For example, the 660 nm-900 nm emitter pair or the 730 nm-900 nm emitter pair may be driven after system start (step 63) and used to measure the arterial oxygen saturation. The previously calculated $SpO_2$ value is considered and a determination is made in step 66 to determine if the $SpO_2$ value is greater than 92%. If the $SpO_2$ value is greater than 92%, then only the 660 nm emitter 24 and the 900 nm 26 emitter are driven to emit light (step 67). The detector signals resulting from the use of the 660 nm emitter 24 and the 900 nm emitter 26 are then processed at step 68 to calculate the next $SpO_2$ value. The 660 nm-900 nm emitter pair is selected to emit light when the previously calculated $SpO_2$ value is greater than 92% because when blood perfused tissue has a high arterial oxygen saturation value (e.g., greater than 92%), then the $SpO_2$ value may be more accurately calculated by using light with a wavelength near 660 nm and light with a wavelength near 900 nm.

If the previously calculated $SpO_2$ value is not greater than 92%, then a determination is made at step 72 to determine if the $SpO_2$ value is less than 68%. If the previously calculated $SpO_2$ value is less than 68%, then only the 730 nm emitter 26 and the 900 nm emitter 28 are driven to emit light (step 74). The detector 30 signals resulting from the use of the 730 nm emitter and the 900 nm emitter are then processed at step 76 to calculate the next $SpO_2$ value. The 730 nm-900 nm emitter pair is selected when the previously calculated $SpO_2$ value is less than 68% because when blood perfused tissue has a low arterial oxygen saturation value (e.g., less than 68%), then the SpO₂ value may be more accurately measured by using light with a wavelength near 730 nm and light with a wavelength near 900 nm.

If the previously calculated SpO₂ value is not less than 68%, then a determination is made at step 78 to determine if the previously calculated SpO₂ value is greater than 89% and equal to or less than 92%. Such a range (e.g., between equal to or greater than 89% and less than 92%) may be chosen because the range may be indicative of the movement of the arterial oxygen towards the transition region (e.g., between 71% and 89%). Accordingly, certain components of the pulse oximeter system 10 may be primed so as to more quickly capture measurements in the transition region. If the previously calculated SpO₂ value is greater than 89% and equal to or less than 92%, then the 660 nm emitter 24, the 730 nm emitter 26, and the 900 nm emitter 28 are driven (step 80). However, the SpO₂ value is calculated in step 82 based on the detector 30 signals resulting from the use of the 660 nm emitter 24 and the 900 nm emitter 28 only. The 730 nm emitter 26 is driven to aid in priming or settling of components of the pulse oximeter system 10, such as emitter temperature and wavelength, filters, ensemble averagers, and so forth. Priming the components in advance aids in preventing start up delays when the signals from the 730 nm emitter 26 begin to contribute to the calculated SpO₂ value.

If the previously calculated SpO₂ value is not greater than 89% and not equal to or less than 92%, then a determination is made at step 84 to determine if the previously calculated SpO₂ value is equal to or greater than 68% and less than 71%. Such a range (e.g., between equal to or greater than 68% and less than 71%) may be chosen because the range may also be indicative of the movement of the arterial oxygen towards the transition region (e.g., between 71% and 89%). If the previously calculated SpO₂ value is equal to or greater than 68% and less than 71%, then the 660 nm emitter 24, the 730 nm emitter 26, and the 900 nm emitter 28 are driven (step 86). However, the SpO₂ value is calculated in step 88 based on the detector 30 signals resulting from the use of the 730 nm emitter 24 and the 900 nm emitter 28 only. The 660 nm emitter 26 is driven to aid in reducing or eliminating any start up delays that may occur when the signals from the 660 nm emitter 24 begin to contribute to the calculated SpO₂ value.

If the previously calculated SpO₂ value is not greater than or equal to 68% and not less than 71% (i.e., between 71% and 89%), then the 660 nm emitter 24, the 730 nm emitter 26, and the 900 nm emitter 28 are driven at step 90. One SpO₂ value is calculated in step 92 based on the detector 30 signals resulting from the use of the 660 nm emitter 24 and the 900 nm emitter 28, and a second SpO₂ value is calculated in step 92 based on the detector 30 signals resulting from the use of the 730 nm emitter 26 and the 900 nm emitter 28. Both of the SpO₂ values calculated in step 92 are then processed in step 94 to arrive at the next SpO₂ value determination. The SpO₂ value determined at step 94 is referred to as the transition SpO₂ value, because the value is inside the transition range where the arterial oxygen saturation is transitioning between high and low values (e.g., greater than or equal to 71% and less than or equal to 89%).

When a SpO₂ value is in the transition range (e.g., when the arterial oxygen saturation is greater than or equal to 71% and less than or equal to 89%), two SpO₂ values are calculated (see step 94 of FIG. 6). One value is referred to as SpO2₆₆₀ and corresponds to the 660 nm-900 nm emitter pair, and a second value is referred to as SpO2₇₃₀ and corresponds to the 730 nm-900 nm emitter pair. In this example flow diagram 62, a single transition SpO₂ value is determined based on these two calculations, and this determination may be made in any suitable manner, such as described in further detail with respect to FIG. 7.

Figure 7:
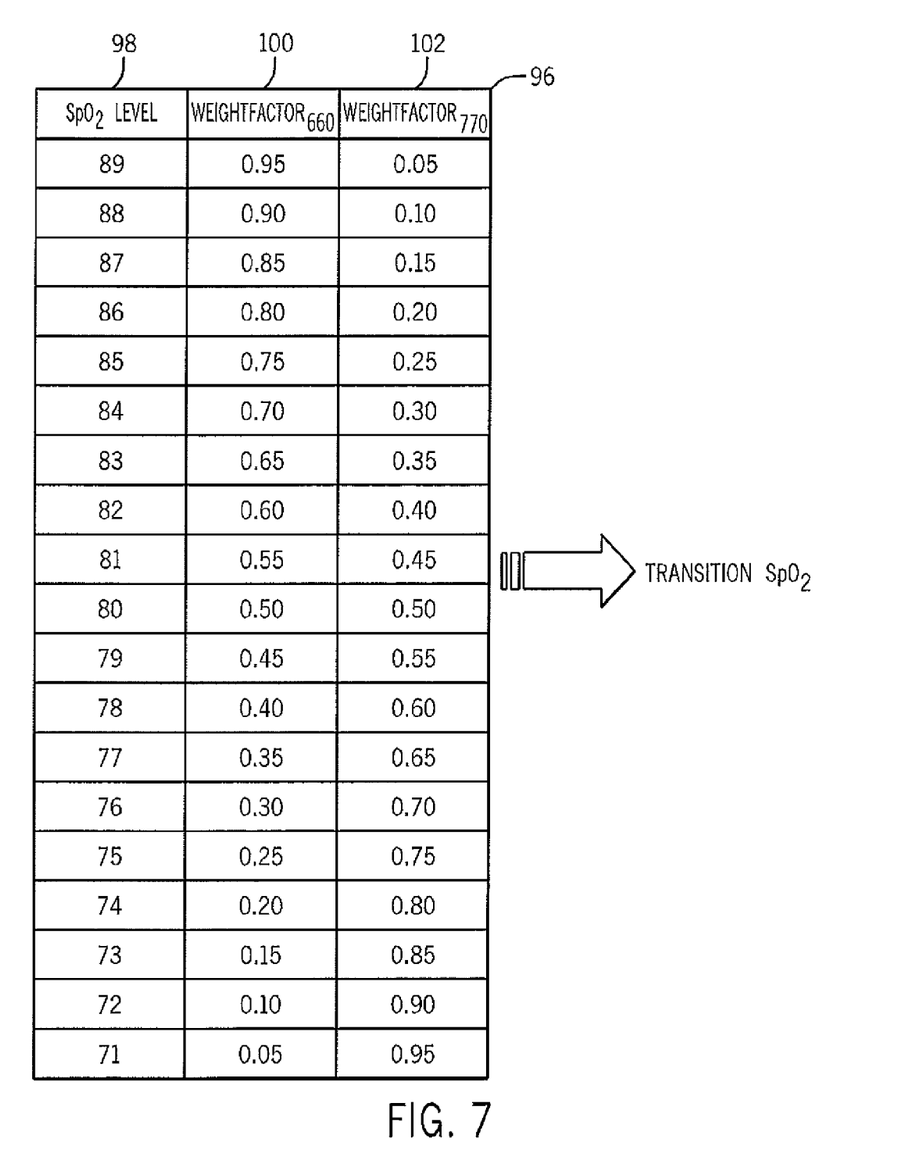
FIG. 7 illustrates another table showing an example of different weight factors and $SpO_2$ levels that may be utilized to calculate the $SpO_2$ for a transition range of operation such as those in FIG. 6.

In one example, FIG. 7 depicts a table 96 of weight factors that may be used, for example, by the methodology described above with respect to FIG. 6, to determine the transition SpO₂ value. In this embodiment, the transition region is found between 71% and 89%. Such slightly broader transition region enables an increase in the number of measurements that use the three wavelengths, and may thus improve measurement accuracy. Indeed, in other embodiments, transition regions such as between 68% to 92%, and between 65% to 95% may be used. As mentioned above with respect to FIG. 5, table 96 may be replaced with an equation, such as an equation including logarithmic and/or exponential functions. Further, the weights may include logarithmic weights, Gaussian weights, and empirical weights.

To determine the transition $Sp_{O2}$ value under this embodiment, the SpO2₆₆₀ value associated with the 660 nm-900 nm emitter pair is first chosen from one of the cells in column 98 (SpO₂ Level) of table 96 and the associated WeightFactor₆₆₀ cell value in column 100 of table 96 is selected. The SpO2₇₃₀ value associated with the 730 nm-900 nm emitter pair is also chosen from one of the cells in column 98 (SpO₂ Level) of table 96 and the associated WeightFactor₇₃₀ cell value in column 102 of table 96 is selected. The following equation may then be used to arrive at the transition SpO₂ value:

$$\text{Transition } SpO_2 = \frac{((SpO2_{660} \times WeightFactor_{660}) + (SpO2_{730} \times WeightFactor_{730}))}{(WeightFactor_{660} + WeightFactor_{730})} \quad (2)$$

The use of the example weight factor table 96 and the weight factor equation (2) may allow for increased accuracy in the transition range because more weight may be given to the SpO₂ value of the emitter pair that is closest to its most accurate usage range. For example, the SpO2₆₆₀ value derived from the use of the emitter pair 660 nm-900 nm may be given more weight when the last calculated SpO₂ value in the transition range is closer to 89%. Similarly, the SpO2₇₃₀ value derived from the use of the 730 nm-900 nm emitter pair may be given more weight when the last calculated SpO₂ value in the transition range is closer to 71%. It is to be understood that other weighing embodiments may be used, for example, logarithmic weighing, Gaussian weighing, and empirical weighing, as mentioned above with respect to FIG. 6.

Logarithmic weighing would replace the weight factor values of table 54 and the weight factor equation with weight factors and a weight equation that may result more weight being given to the various SpO₂ values based on the logarithmic scale that was chosen. Gaussian weighing would replace the weight factor values of table 54 and the weight factor equation with weight factors and a weight equation that may result in more weight be given to the SpO₂ values based on the Gaussian scale that was chosen. Empirical weighing would replace the weight factor values of table 54 and the weight factor equation with weight factors and a weight equation derived from empirical studies of patient tissue.

Figure 8:
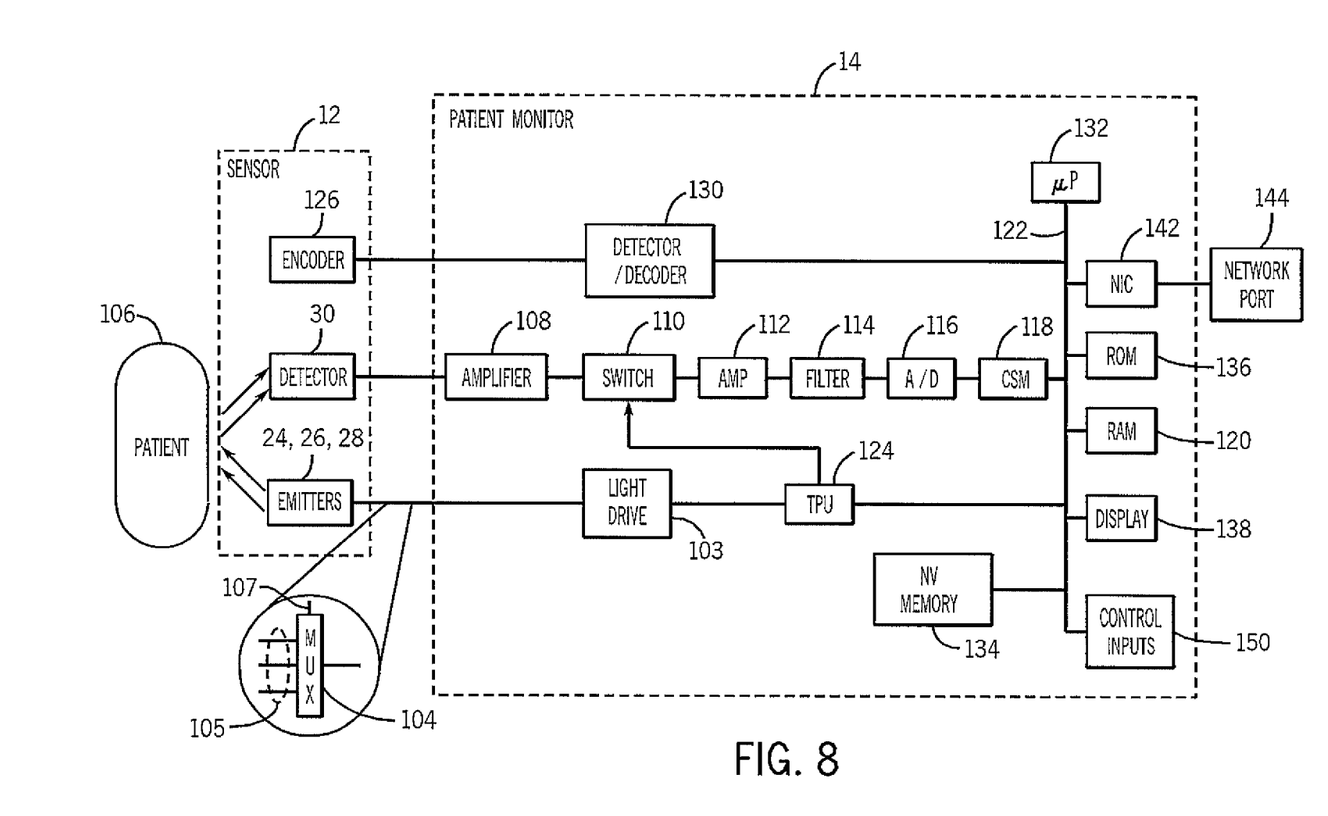
FIG. 8 depicts the block diagram of the monitor connected to the sensor of FIG. 2A or 2B in accordance with an embodiment of the present disclosure.

FIG. 8 depicts a block diagram of one embodiment of a pulse oximeter that may be configured to implement certain embodiments. In one embodiment, light drive circuitry 103 may drive all three of the emitters 24, 26, 28 directly. In another embodiment, light drive circuitry 103 is designed to drive only two emitters and a multiplexer 104 may be used. In this embodiment, multiplexer 104 may convert the control signals sent by the light drive circuitry 103 into a series of signals which may drive the three emitters 24, 26, 28. Accordingly, the multiplexer 104 may include three output lines 105 suitable for driving the three emitters 24, 26, and 29. Further, the multiplexer 104 may include a control line 106 useful for selecting which emitter(s) are to be driven. Light from emitters 24, 26, 28 passes into a patient's blood perfused tissue 106 and is detected by detector 30. The signals corresponding to the light detected by detector 30 may be passed through an amplifier 108, a switch 110, a post-switch amplifier 112, a low band filter 114, and an analog-to-digital converter 116. The digital data may then be stored in a queued serial module (QSM) 118 for later downloading to RAM 120 as QSM 118 fills up.

In one embodiment, also connected to a bus 122 may be a time processing unit (TPU) 124 that may provide timing control signals to light drive circuitry 103. The sensor 12 may also contain an encoder 126 that may include encryption coding that prevents a disposable part of the sensor 12 from being recognized by a detector/decoder 130 that is not able to decode the encryption. In some embodiments, the encoder 126 and/or the detector/decoder 130 may not be present. Additionally or alternatively, a processor 132 may encode and/or decode processed sensor data before transmission of the data to the patient monitor 14.

Nonvolatile memory 134 may store caregiver preferences, patient information, or various parameters such as a table of weight factors, discussed above with respect to FIGS. 5 and 7, which may be used during the operation of the monitor 14. Software for performing the configuration of the monitor 14 and for carrying out the techniques described herein may also be stored on the nonvolatile memory 134, or may be stored on the ROM 136. The data stored in nonvolatile memory 134 may be displayed by display 138 and manipulated through control inputs 140. A network interface card (NIC) 142 may use a network port 144 to enable communications between the patient monitor 14 and other devices.

In various embodiments, based at least in part upon the value of the received signals corresponding to the light detected by detector 30 as explained in further detail with respect to FIGS. 9A, 9B, 9C below, the microprocessor 132 may calculate a physiological parameter of interest using various algorithms. These algorithms may utilize coefficients, which may be empirically determined, corresponding to, for example, the wavelengths of light used. In one embodiment microprocessor 132 may use certain algorithms that calculate the final $SpO_2$ value. In this embodiment the algorithms may contain the weight factor tables 54 of FIGS. 6 and 96 of FIG. 7, and use weight factor equations (1) and (2) to calculate the oxygen saturation. In another embodiment, microprocessor 132 may use an averaging algorithm that averages various oxygen saturation values into a single oxygen saturation value. In yet another embodiment microprocessor 132 may use an arbitration algorithm that arbitrates among various oxygen saturation values and return a single oxygen saturation value. Furthermore, any number of methods or algorithms may be used to determine, for example, a patient's pulse rate, oxygen saturation, and hemoglobin levels, among others.

As mentioned above with respect to FIG. 8, the disclosed techniques may include detector signals that may correspond to certain wavelengths of light detected by the detector at particular points in time. FIGS. 9A, 9B, and 9C depict an example set of detector signals that may be converted by the microprocessor into values corresponding to the detected wavelengths of light as well as to the point in time when the wavelengths of light were detected. More specifically, FIG. 9A depicts a detector signal that may be used by the microprocessor when only one emitter pair is being driven. In this example, the detector is detecting light emitted by the 660 nm-900 nm emitter pair. The 660 nm-900 nm pair may be used, for example, when the arterial oxygen saturation is in the high saturation range. The first on signal (+V) 146 of FIG. 9A denotes that the detected light was emitted by the 660 nm emitter. The first off signal (0V) 148 denotes that the 660 nm emitter was then turned off. It is to be understood that due to, for example, a slight leakage of ambient light, the off or "dark time" signal may be slightly larger than 0V. The next on signal (+V) 146 denotes that the detected light was emitted by the 900 nm emitter. The next off signal (0V) 148 denotes that the 900 nm emitter was turned off, and so on. Using the signal of FIG. 9A the microprocessor may properly account for the wavelength of light that was detected as well as for the time when the light was detected. The microprocessor may then properly calculate the $SpO_2$ value as well other physiologic measures from the detected light signals.

Figure 9A:
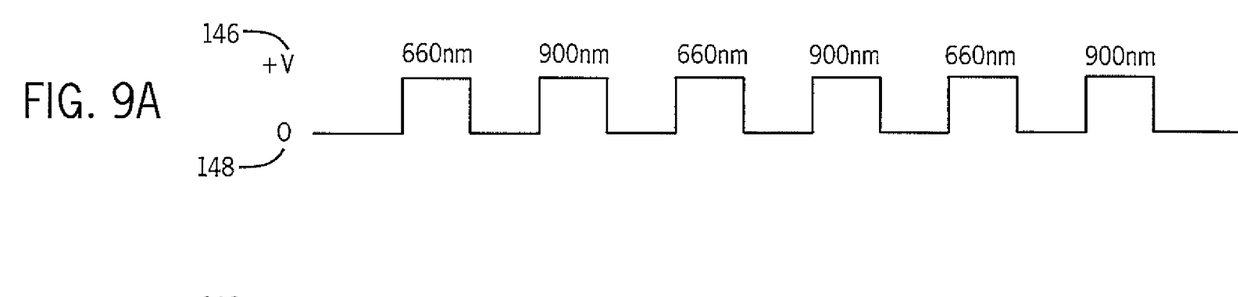
FIG. 9A depicts an example set of signals that may be received by the detector when a single light emitter pair is in use.
Figure 9B:
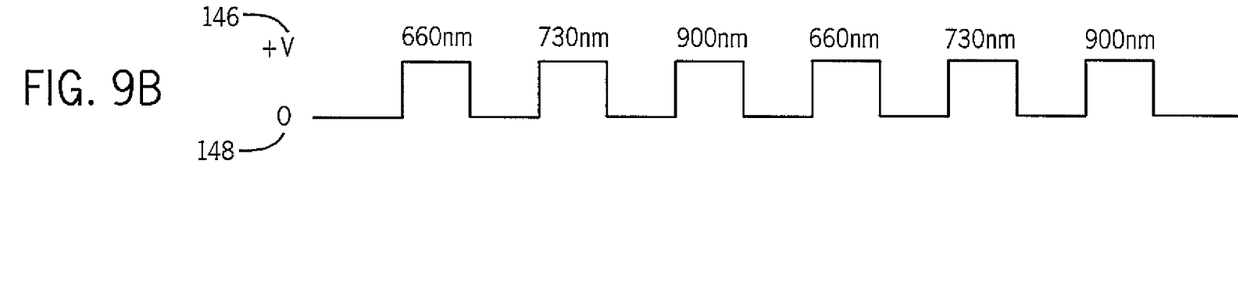
FIG. 9B depicts an example set of signals that may be received by the detector when two light emitter pairs are in use.

FIG. 9B shows an example of a detector signal that may be used by the microprocessor when two light emitter pairs are being driven. In this example, the 660 nm-900 nm and the 730 nm-900 nm emitter pairs are both being driven to emit light. Two light emitter pairs may be used, for example, when the arterial oxygen saturation is in the transition region. The first on signal (+V) 146 of FIG. 9B shows that the detected light was emitted by the 660 nm emitter and that the 660 nm emitter was subsequently turned off (0V) 148. The next on signal (+V) 146 shows that the detected light was emitted by the 730 nm emitter and that the 730 nm emitter was subsequently turned off (0V) 148. The next on signal (+V) 146 shows that the detected light was emitted by the 900 nm emitter and that the 900 nm emitter was subsequently turned off (0V) 148, and so on. By using the signal of FIG. 9B the microprocessor may properly account for the wavelengths of light detected when two emitter pairs are used (e.g., the 660 nm-900 nm and the 730 nm-900 nm emitter pairs). The microprocessor may then use this information to properly derive the $SpO_2$ value as well other physiologic measures from the detected light signals.

Figure 9C:
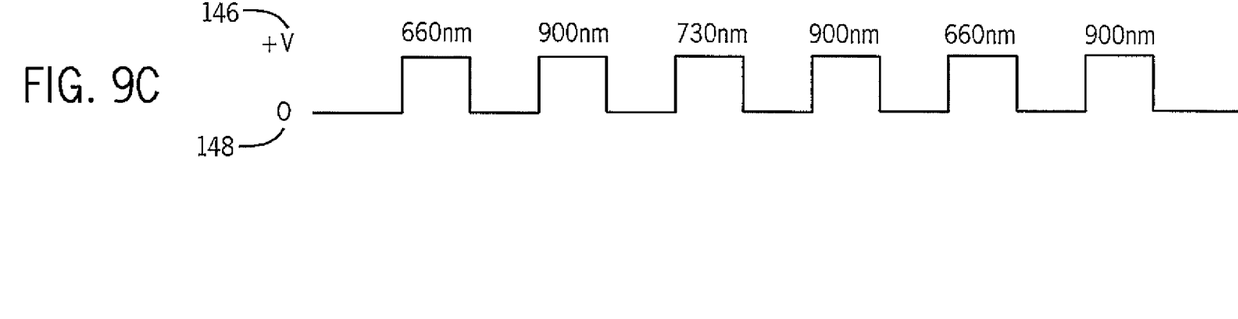
FIG. 9C depicts another example set of signals that may be received by the detector when two light emitter pairs are in use.

FIG. 9C shows another example of a detector signal that may be used by the microprocessor when two light emitter pairs are being driven. In this example, the 660 nm-900 nm and the 730 nm-900 nm emitter pairs are also being driven to emit light. Two light emitter pairs may be used, for example when the arterial oxygen saturation is in the transition region. The first on signal (+V) 146 of FIG. 9C shows that the detected light was emitted by the 660 nm emitter and that the 660 nm emitter was subsequently turned off (0V) 148. The next on signal (+V) 146 shows that the detected light was emitted by the 900 nm emitter and that the 900 nm emitter was subsequently turned off (0V) 148. The next on signal (+V) 146 shows that the detected light was emitted by the 730 nm emitter and that the 730 nm emitter was subsequently turned off (0V) 148, and so on. The microprocessor may use the signal of FIG. 9C to properly account for the detected wavelengths of light when two emitter pairs are used (e.g., the 660 nm-900 nm and the 730 nm-900 nm emitter pairs). The microprocessor may then use this information to properly derive the $SpO_2$ value as well other physiologic measures from the detected light signals.

It is to be understood that the modulation examples of FIGS. 9A, 9B, and 9C, may be modulated by using modulation techniques other than time division multiplexing (TDM). Other example techniques that may be used include Frequency Division Multiplexing (FDM), and/or spread spectrum/code division multiple access (CDMA) techniques.

Indeed, the pulse oximeter system 10 may include a variety of modulation techniques useful for driving the emitters 24, 26, and 28 and observing the resultant light.

What is claimed is:

1. A method of sensing physiologic parameters of a patient, the method comprising:

determining the patient's arterial oxygen saturation level;

if the patient's arterial oxygen saturation level is in a high range, driving only a first set of emitters on a sensor configured to substantially optimize physiologic measurements in patients having high arterial oxygen saturation levels and calculating a new arterial oxygen saturation level of the patient using data generated using only the first set of emitters;

if the patient's arterial oxygen saturation level is in a low range, driving only a second set of emitters on the sensor configured to substantially optimize physiologic measurements in patients having low arterial oxygen saturation levels and calculating the new arterial oxygen saturation level of the patient using data generated using only the second set of emitters; and if the patient's arterial oxygen saturation level is in a transition range between the high range and the low range, driving the first and second sets of emitters on the sensor and calculating the new arterial oxygen saturation level of the patient using data generated using both the first and second set of emitters.

2. The method of claim 1, wherein the high range comprises a range of arterial oxygen saturation greater than 84%.

3. The method of claim 1, wherein the transition range comprises a range of arterial oxygen saturation between 85% and 76%.

4. The method of claim 1, wherein the high range comprises a range of arterial oxygen saturation greater than 89%, and wherein the low range comprises a range of arterial oxygen saturation less than 71%.

5. The method of claim 1, wherein the transition range comprises a range of arterial oxygen saturation between 90% and 70%.

6. The method of claim 1, comprising determining a final SpO$_2$ value by using a weight factor table, using a weight factor equation, or a combination thereof.

7. The method of claim 1, comprising driving the first and the second set of emitters after a system start.

8. The method of claim 1, comprising driving the first or the second set of emitters after a system start.

9. The method of claim 1, comprising, if the patient's arterial oxygen saturation level is in an intermediate range between the high range and the transition range, driving both the first and the second set of emitters on the sensor, processing signals generated using both the first and the second set of emitters, and calculating the new arterial oxygen saturation level using signals generated using only the first set of emitters.

10. A system, comprising:

a sensor comprising:

a first emitter pair configured to emit at least two wavelengths configured to substantially optimize physiologic measurements in patients having high arterial oxygen saturation levels; and a second emitter pair configured to emit at least two wavelengths configured to substantially optimize physiologic measurements in patients having low arterial oxygen saturation levels; and a monitor comprising:

a processor configured to receive one or more signals from the sensor and to determine a patient's arterial oxygen saturation based at least in part upon the one or more signals; and drive circuitry configured to drive only the first emitter pair in response to a determination that the patient's arterial oxygen saturation is in a high range, to drive only the second emitter pair in response to a determination that the patient's arterial oxygen saturation is in a low range, and to drive the first and the second emitter pairs in response to a determination that the patient's arterial oxygen saturation level is in a transition region between the high range and the low range; and wherein the processor is configured to determine a new value of the patient's arterial oxygen saturation using data generated using only the first emitter pair in response to the determination that the patient's arterial oxygen saturation is in the high range, to determine the new value of the patient's arterial oxygen saturation using data generated using only the second emitter pair in response to the determination that the patient's arterial oxygen saturation is in the low range, and to determine the new value of the patient's arterial oxygen saturation using data generated using both the first and the second emitter pairs in response to the determination that the patient's arterial oxygen saturation is in the transition region.

11. The system of claim 10, wherein the drive circuitry is configured to drive the first and the second emitter pairs in response to a determination that the patient's arterial oxygen saturation is in a high transition range between the high range and the transition region, and wherein signals generated using the second emitter pair are processed by the monitor to prime components of the monitor, and wherein the processor is configured to calculate the new value of the patient's arterial oxygen saturation using signals generated using only the first emitter pair.

12. The system of claim 10, wherein the drive circuitry is configured to drive the first and the second emitter pairs in response to a determination that the patient's arterial oxygen saturation is in a low transition range between the low range and the transition region, and wherein signals generated using the first emitter pair are processed by the monitor to prime components of the monitor, and wherein the processor is configured to calculate the new value of the patient's arterial oxygen saturation using signals generated using only the second emitter pair.

13. The system of claim 10, wherein the processor is configured to determine a first value and a second value of the patient's arterial oxygen saturation using signals generated using the first emitter pair and the second emitter pair, respectively, and to determine the new value of the patient's arterial oxygen saturation based at least in part upon the first and the second values when the patient's arterial oxygen saturation is in the transition region.

14. The system of claim 13, wherein the processor is configured to determine the new value of the patient's arterial oxygen saturation using a weight factor table and a weight factor equation.

15. The system of claim 14, wherein the processor is configured to determine a first weight factor for the first value of the patient's arterial oxygen saturation and a second weight factor for the second value of the patient's arterial oxygen saturation from the weight factor table based at least in part upon the first and the second values of the patient's arterial oxygen saturation, respectively.

16. The system of claim 15, wherein the first weight factor is greater than the second weight factor if the first value of the patient's arterial oxygen saturation is closer to the high range than the second value of the patient's arterial oxygen saturation is to the low range.

17. A patient monitor comprising:
drive circuitry configured to drive a first emitter, a second emitter, and a third emitter of a sensor disposed about a patient, wherein the first, second, and third emitters are configured to emit a first wavelength, a second wavelength, and a third wavelength, respectively; and
a processor configured to:
calculate an oxygen saturation value of the patient based at least in part upon one or more signals received from the sensor;
cause the drive circuitry to drive only the first and second emitters in response to a determination that the oxygen saturation value is above a first threshold, to drive only the second and third emitters in response to a determination that the oxygen saturation value is below a second threshold that is less than the first threshold, and to drive the first, second, and third emitters in response to a determination that the oxygen saturation value is in a transition region between the first and the second thresholds; and
calculate a new oxygen saturation value using signals generated using only the first and second emitters in response to the determination that the oxygen saturation is above the first threshold, calculate the new oxygen saturation value using signals generated using only the second and third emitters in response to the determination that the oxygen saturation value is below the second threshold, and calculate the new oxygen saturation value using signals generated using the first, second, and third emitters in response to the determination that the oxygen saturation value is in the transition region.

18. The patient monitor of claim 17, wherein the processor is configured to determine a first oxygen saturation value using signals generated using the first and second emitters, to determine a second oxygen saturation value using signals generated using the second and third emitters, and to determine the new oxygen saturation value using both the first and the second oxygen saturation values when the oxygen saturation value is in the transition region.

19. The patient monitor of claim 18, wherein the processor is configured to determine the new oxygen saturation value using logarithmic weighting, Guassian weighting, empirical weighting, or a combination thereof.

20. The patient monitor of claim 18, wherein the processor is configured to determine the new oxygen saturation value using a weight factor table and a weight factor equation.

21. The patient monitor of claim 20, wherein the processor is configured to determine a first weight factor for the first value of the patient's arterial oxygen saturation and a second weight factor for the second value of the patient's arterial oxygen saturation from the weight factor table based at least in part upon the first and the second values of the patient's arterial oxygen saturation, respectively.

22. The system of claim 17, wherein the drive circuitry is configured to drive the first, second, and third emitters in response to a determination that the oxygen saturation value is greater than the second threshold and is less than a minimum threshold of the transition region, and wherein signals generated using the first emitter are processed by the patient monitor to prime components of the patient monitor, and wherein the processor is configured to calculate the new oxygen saturation value using signals generated using only the second and third emitters.

23. The system of claim 17, wherein the drive circuitry is configured to drive the first, second, and third emitters in response to a determination that the oxygen saturation value is less than the first threshold and is greater than a maximum threshold of the transition region, and wherein signals generated using the third emitter are processed by the patient monitor to prime components of the patient monitor, and wherein the processor is configured to calculate the new oxygen saturation value using signals generated using only the first and second emitters.

* * * * *